US011839744B2

(12) United States Patent
Grosman et al.

(10) Patent No.: US 11,839,744 B2
(45) Date of Patent: Dec. 12, 2023

(54) AUTOMATED SUPER BOLUS GENERATION (71) Applicant: Medtronic MiniMed, Inc., Northridge, CA (US)

(72) Inventors: Benyamin Grosman, Winnetka, CA (US); Louis J. Lintereur, Boise, ID (US); Anirban Roy, Agoura Hills, CA (US); Neha J. Parikh, West Hills, CA (US); Di Wu, Glendale, CA (US); Patrick E. Weydt, Moorpark, CA (US); David Dunleavy, West Hills, CA (US); Ali Dianaty, Porter Ranch, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 484 days.

(21) Appl. No.: 17/179,070

(22) Filed: Feb. 18, 2021

(65) Prior Publication Data
US 2022/0257858 A1   Aug. 18, 2022

(51) Int. Cl.
*A61M 5/172* (2006.01)
(52) U.S. Cl.
CPC ........ *A61M 5/1723* (2013.01); *A61M 2205/52* (2013.01); *A61M 2230/201* (2013.01)
(58) Field of Classification Search
CPC .... A61M 2005/14208; A61M 2205/52; A61M 2230/201; A61M 5/14276; A61M 5/1723
See application file for complete search history.

(56) References Cited

U.S. PATENT DOCUMENTS

| | | |
|---|---|---|
| 4,562,751 A | 1/1986 | Nason et al. |
| 4,685,903 A | 8/1987 | Cable et al. |
| 5,080,653 A | 1/1992 | Voss et al. |
| 5,097,122 A | 3/1992 | Colman et al. |
| 5,505,709 A | 4/1996 | Funderburk et al. |
| 6,088,608 A | 7/2000 | Schulman et al. |
| 6,119,028 A | 9/2000 | Schulman et al. |
| 6,485,465 B2 | 11/2002 | Moberg et al. |
| 6,554,798 B1 * | 4/2003 | Mann .................. A61M 5/172 604/67 |
| 6,558,320 B1 | 5/2003 | Causey, III et al. |
| 6,558,351 B1 | 5/2003 | Steil et al. |
| 6,589,229 B1 | 7/2003 | Connelly et al. |

(Continued)

*Primary Examiner* — Quynh-Nhu H. Vu
(74) *Attorney, Agent, or Firm* — Weaver Austin Villeneuve & Sampson LLP (57) ABSTRACT

Techniques related to automatically generating a super bolus may include determining an amount of an augmented meal bolus to be delivered to a patient for regulating the patient's glycemic response to a meal. The amount of the augmented meal bolus may exceed a sufficient amount for counteracting a glucose level increase caused by the meal. In some embodiments, the techniques may further include determining a duration of a postprandial reduction period during which basal dosage deliveries to the patient are to be reduced. In some other embodiments, the techniques may further include delivering the augmented meal bolus to the patient prior to determining whether or not to cause reduction of basal dosage deliveries. More specifically, a glucose level of the patient may be obtained after delivery of the augmented meal bolus, and the obtained glucose level may be used to determine whether to reduce basal dosage deliveries.

20 Claims, 5 Drawing Sheets (56) References Cited

U.S. PATENT DOCUMENTS

| | | | |
|---|---|---|---|
| 6,641,533 B2 | 11/2003 | Causey, III et al. | |
| 6,659,980 B2 | 12/2003 | Moberg et al. | |
| 6,740,072 B2 * | 5/2004 | Starkweather | A61M 5/1723 |
| | | | 604/67 |
| 6,752,787 B1 | 6/2004 | Causey, III et al. | |
| 6,817,990 B2 | 11/2004 | Yap et al. | |
| 6,827,702 B2 * | 12/2004 | Lebel | A61M 5/14276 |
| | | | 604/67 |
| 6,932,584 B2 | 8/2005 | Gray et al. | |
| 7,323,142 B2 | 1/2008 | Pendo et al. | |
| 7,402,153 B2 | 7/2008 | Steil et al. | |
| 7,621,893 B2 | 11/2009 | Moberg et al. | |
| 7,704,226 B2 * | 4/2010 | Mueller, Jr. | A61M 5/14244 |
| | | | 604/65 |
| 7,959,598 B2 * | 6/2011 | Estes | A61M 5/1413 |
| | | | 604/503 |
| 8,674,288 B2 | 3/2014 | Hanson et al. | |
| 9,330,237 B2 * | 5/2016 | Cohen | A61B 5/7275 |
| 2011/0106050 A1 * | 5/2011 | Yodfat | A61M 5/1723 |
| | | | 604/504 |
| 2014/0066887 A1 | 3/2014 | Mastrototaro et al. | |
| 2014/0066889 A1 | 3/2014 | Grosman et al. | |

\* cited by examiner

AUTOMATED SUPER BOLUS GENERATION

TECHNICAL FIELD

The disclosure is generally related to methods and devices for delivering therapy to a patient, such as insulin for diabetes therapy.

BACKGROUND

A patient may use insulin therapy to manage type I or type II diabetes. Insulin therapy may include use of insulin infusion systems for delivering or dispensing insulin. An insulin infusion system may include an infusion device which typically includes a small motor and drive train components configured to deliver insulin from a reservoir into the body of the patient, e.g., via a percutaneous needle or a cannula placed in the subcutaneous tissue. Insulin infusion systems may facilitate management of diabetes for some patients.

SUMMARY

The present disclosure relates to techniques for automated super bolus generation. The techniques may be practiced using systems; processor-implemented methods; and non-transitory processor-readable storage media storing instructions which, when executed by one or more processors, cause performance of automated super bolus generation.

In some embodiments, automated super bolus generation may involve determining an amount of an augmented meal bolus to be delivered to a patient for regulating the patient's glycemic response to a meal. The amount of the augmented meal bolus may exceed a sufficient amount for counteracting a glucose level increase caused by the meal. Automated super bolus generation may also involve determining a duration of a postprandial reduction period during which basal dosage deliveries to the patient are to be reduced. After determining the amount of the augmented meal bolus and the duration of the postprandial reduction period, the augmented meal bolus may be delivered to the patient in the determined amount, and basal dosage deliveries to the patient may be reduced for the duration of the postprandial reduction period.

In some embodiments, automated super bolus generation may involve determining an amount of an augmented meal bolus to be delivered to a patient for regulating the patient's glycemic response to a meal. The amount of the augmented meal bolus may exceed a sufficient amount for counteracting a glucose level increase caused by the meal. The augmented meal bolus may be delivered to the patient in the determined amount. After delivery of the augmented meal bolus, a glucose level of the patient may be obtained. Based on the glucose level, basal dosage deliveries to the patient may be reduced.

The details of one or more examples are set forth in the accompanying drawings and the description below. Other features, object, and advantages will be apparent from the description and drawings, and from the claims.

DETAILED DESCRIPTION

The present disclosure relates to automated super bolus generation. A super bolus may include an augmented bolus dosage followed by a period of reduced (e.g., to a zero or non-zero amount or rate) basal dosage deliveries. For example, in the context of insulin delivery related to a meal, an augmented meal bolus enables more insulin to be available for counteracting a rapid increase in glucose level caused by consumption of the meal, and postprandial reduction of basal dosage deliveries decreases the likelihood of insulin stacking. Thus, a super bolus enables regulation of a physiological condition (e.g., glucose concentration) within a tighter range for increased stability of the physiological condition. Furthermore, automation of super bolus generation enables such regulation with increased accuracy, efficiency, and convenience.

Although the techniques disclosed herein are explained in the context of insulin infusion systems, it should be appreciated that the disclosed techniques are not limited to insulin infusion systems. For example, the techniques may be implemented in an equivalent manner in the context of therapy delivery devices that are not configured for insulin infusion. Furthermore, it should be appreciated that the techniques disclosed herein can be practiced with one or more types of insulin (e.g., fast-acting insulin, intermediate-acting insulin, and/or slow-acting insulin). Thus, terms such as "basal insulin" and "bolus insulin" do not necessarily denote different types of insulin. For example, fast-acting insulin may be used for both basal dosages and bolus dosages.

Figure 1:
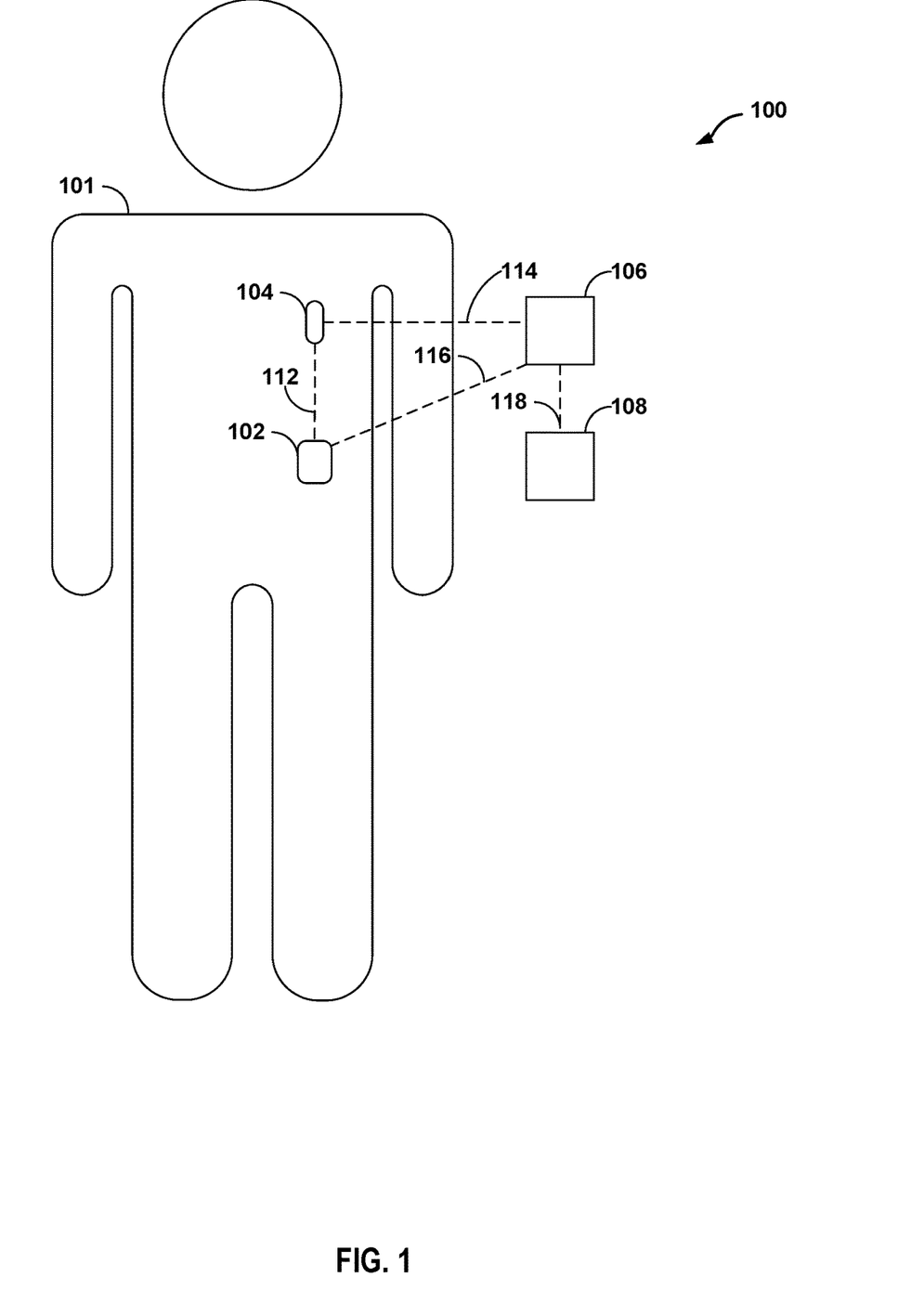
FIG. 1 is a conceptual diagram illustrating an example infusion system.

FIG. 1 is a conceptual diagram illustrating an example infusion system 100. Infusion system 100 may be configured to deliver a super bolus to patient 101. Infusion system 100 may include infusion device 102, monitoring device 104, computing device 106, and user interface 108. Infusion device 102, monitoring device 104, computing device 106, and/or user interface 108 may be disposed on the same device or on different devices. In some examples, infusion system 100 or one or more components thereof may include a portable device and/or an implantable medical device. In some examples, infusion system 100 may include components similar to those described in, for example, commonly assigned U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893, each of which is incorporated herein by reference in its entirety.

Infusion device 102 is configured to deliver a therapeutic substance (e.g., insulin) to patient 101. Infusion device 102 may be secured to patient 101 (e.g., to the body or clothing of patient 101) or implanted in the body of the patient 101. Infusion device 102 may be separate from or incorporated with monitoring device 104, computing device 106, and/or user interface 108.

In some examples, infusion device 102 may include a reservoir, an actuator, a delivery mechanism, and a cannula. The reservoir may be configured to store a predetermined amount of the therapeutic substance. In some examples, the reservoir may be refillable or replaceable. The actuator may be configured to drive the delivery mechanism. In some examples, the actuator may include a motor, such as an electric motor. The delivery mechanism may be configured to move the therapeutic substance from the reservoir through the cannula. In some examples, the delivery mechanism may include a pump or a plunger. The cannula may facilitate a fluidic connection between the reservoir and the body of patient 101. In some examples, the cannula and/or a needle may facilitate delivery of the therapeutic substance to a tissue layer, vein, or body cavity of patient 101. In some examples, infusion device 102 may include additional components, such as a power supply and/or a transceiver for communication with other devices. During operation, the actuator, in response to a signal (e.g., a command signal), may drive the delivery mechanism, thereby causing the therapeutic substance to move from the reservoir, through the cannula, and into the body of patient 101.

Monitoring device 104 is configured to detect a physiological condition (e.g., a glucose concentration level) of patient 101. Monitoring device 104 may be secured to the body of patient 101 (e.g., to the skin of patient 101 via an adhesive) and/or at least partially implanted into the body of patient 101. Monitoring device 104 may be separate from or incorporated with infusion device 102, computing device 106, and/or user interface 108. Depending on the particular location or configuration, monitoring device 104 may be in contact with biological matter (e.g., interstitial fluid and/or blood) of patient 101. In some examples, monitoring device 104 may include one or more electrodes configured to generate a signal (e.g., a sensor data signal) indicative of a concentration of a biological marker, such as a glucose level of patient 101. In some examples, monitoring device 104 may be a continuous glucose monitoring device that senses glucose and communicates with one or more other devices such as infusion device 102 and/or computing device 106.

As illustrated in FIG. 1, monitoring device 104 may be communicatively coupled (e.g., connected) to computing device 106 via link 114 or infusion device 102 via link 112. Links 114 and 112 may each be any suitable wired or wireless connection. For example, monitoring device 104 may include a communications interface, such as an Ethernet card, a radio frequency transceiver, cellular transceiver, a Bluetooth® interface card, USB interface, and/or any other type of device that can send and/or receive information. Monitoring device 104 may generate a signal (e.g., output signal) representative of the physiological condition of patient 101, e.g., the concentration of the biological marker, and may provide the signal to computing device 106 via link 114 or infusion device 102 via link 112. In some examples, monitoring device 104 may be configured to condition the signal prior to providing the signal to computing device 106 or infusion device 102. Conditioning may include, but is not limited to, amplification, filtering, attenuation, isolation, and/or transformation. In some examples, monitoring device 104 may provide an unconditioned signal to computing device 106 or infusion device 102, either of which may condition the signal.

Monitoring device 104 may include an electrochemical sensor, an electrical sensor, and/or an optical sensor. In examples in which monitoring device 104 includes an electrochemical sensor, the electrochemical sensor may be configured to, in response to the interaction or binding of the biological marker to a substrate, generate an electronic signal based on a potential, conductance, and/or impedance of the substrate. The substrate may include a material selected to interact with a particular biomarker, such as glucose. The potential, conductance, and/or impedance may be proportional to a concentration of the particular biomarker.

In examples in which monitoring device 104 includes an electronic sensor, the electronic sensor may be configured to, in response to an electrical biosignal, generate an electronic signal based on an amplitude, frequency, and/or phase of the electrical biosignal. The electrical biosignal may include a change in electric current produced by the sum of an electrical potential difference across a tissue, such as the nervous system, of patient 101. In some examples, the electrical biosignal may include portions of a potential change produced by the heart of patient 101 over time, e.g., recorded as an electrocardiogram, that are indicative of a glucose level of patient 101.

In examples in which monitoring device 104 includes an optical sensor, the optical sensor may be configured to, in response to the interaction or binding of the biological marker to a substrate, generate an electronic signal based on change in luminance of the substrate. For example, the substrate may include a material selected to fluoresce in response to contact with a selected biomarker, such as glucose. The fluorescence may be proportional to a concentration of the selected biomarker.

Computing device 106 may be operatively coupled to infusion device 102 and/or monitoring device 104 to control operation of infusion device 102 and/or monitoring device 104. Computing device 106 may be secured to patient 101 (e.g., to the body or clothing of patient 101), at least partially implanted into the body of patient 101, or remotely located from patient 101. Computing device 106 may be separate from or incorporated with infusion device 102, monitoring device 104, and/or user interface 108.

Computing device 106 may be any suitable computing device, such as a smartphone, a computerized wearable device (e.g., a watch, eyewear, ring, or necklace), a tablet computer, a laptop computer, or a desktop computer. Computing device 106 may be a consumer device configured to perform the techniques of this disclosure by executing program instructions, and/or computing device 106 may be a special purpose device (e.g., a remote control device) provided by, for example, the manufacturer of infusion device 102. Computing device 106 may include various types of fixed function and/or programmable processing circuitry or other hardware, including, but not limited to, microprocessors, controllers, digital signal processors (DSPs), application specific integrated circuits (ASICs), field-programmable gate arrays (FPGAs), or equivalent discrete or integrated logic circuitry, as well as combinations of such components. The term "processing circuitry" may generally refer to any of the foregoing logic circuitry, alone or in combination with other logic circuitry, or any other equivalent circuitry. In some examples, computing device 106 includes hardware that can be configured to execute firmware and/or software that sets forth one or more of the techniques described herein. For example, computing device 106 may be configured to implement functionality, process instructions, or both for execution of processing instructions stored within one or more storage components.

In some examples, sensor data from monitoring device 104 is received by processing circuitry of computing device 106. The processing circuitry may condition (or further condition) the received sensor data, for example, as described above.

In some examples, computing device 106 may be configured to receive user input, e.g., a meal indication, via user interface 108. An example meal indication may include a type of meal (e.g., breakfast, lunch, dinner, snack, or other meal), an approximate amount of carbohydrates consumed/to be consumed, and/or other information that may affect an amount of insulin to be delivered as a meal bolus. In response to receiving the user input, the processing circuitry of computing device 106 may determine a meal bolus amount. The meal bolus amount may be an amount of insulin that is sufficient for counteracting an increase in glucose level caused by consumption of a meal (e.g., a certain amount of carbohydrates).

In some examples, computing device 106 is operatively coupled (e.g., connected) to infusion device 102 via link 116. Link 116 may be the same or similar to link 114 discussed above. Thus, computing device 106 may control operation of infusion device 102 via link 116. For example, computing device 106 may generate one or more signals (e.g., a command signal) that cause infusion device 102 to deliver insulin to patient 101, e.g., as a basal dosage and/or a bolus dosage.

In some examples, computing device 106 may receive from infusion device 102 data associated with insulin delivery (e.g., insulin delivery data). Insulin delivery data may include, but is not limited to, a type of insulin being delivered, historical insulin delivery rates and/or amounts, current insulin delivery rate and/or amount, and/or user input affecting insulin delivery. In some examples, the insulin delivery data is received by processing circuitry of computing device 106. The processing circuitry of computing device 106 (and/or processing circuitry of one or more other devices of infusion system 100) may determine a predicted change in concentration of the biological marker, e.g., a glucose level, based on the insulin delivery data.

Computing device 106 may be operatively coupled (e.g., connected) to user interface 108 (e.g., via link 118 or some other wired or wireless connection if user interface 108 is implemented on a separate device from computing device 106). In some examples, computing device 106 and user interface 108 may be integrated into a single device, such as a smart phone, tablet computer, laptop computer, or the like. User interface 108 may be a graphical user interface (GUI) and/or may be implemented using a display device, a keyboard, a touchscreen, a speaker, a microphone, a gyroscope, an accelerometer, a vibration motor, and/or the like. Computing device 106 may generate information that is communicated to a user (e.g., patient 101, a caregiver, or a clinician) via user interface 108 as tactile output, audio output, video output, or the like. In this way, user interface 108 may notify a user of sensor data (e.g., a glucose level) and/or insulin delivery data (e.g., rates of historic, current, or future insulin delivery). As one example, computing device 106 may receive an indication of a change in insulin delivery from infusion device 102 and cause user interface 108 to present an alert indicative of the change in insulin delivery. The alert may include any type of information understandable by a human. For example, the alert may include information representative of the change in insulin delivery that can be displayed on a display device of user interface 108. In some examples, the display device of user interface 108 may be included in a mobile device of the user, and the information representative of the change in insulin delivery may be a text, email, system notification, push notification, or web application notification.

In some examples, computing device 106 may receive tactile input, kinetic input, audio input, optical input, or the like from a user via user interface 108. Thus, user interface 108 may receive user input from a user and send the user input to computing device 106. The user input (e.g., user data) may include, for example, a requested change in insulin delivery, a glucose level, and a meal indication.

In some examples, infusion device 102, monitoring device 104, and computing device 106 are configured to utilize a closed-loop control system for delivering insulin to patient 101. Example insulin infusion systems and techniques using closed-loop control systems may include, but are not limited to, the systems and techniques described in commonly assigned U.S. Pat. Nos. 6,740,072; 6,827,702; 7,323,142; and 7,402,153; and United States Patent Application Publication Nos.: 2014/0066887 and 2014/0066889, each of which is incorporated herein by reference in its entirety. For example, monitoring device 104 may be configured to detect a condition of the patient, such as a glucose level. Infusion device 102 may be configured to deliver insulin to patient 101 based on the detected condition. Monitoring device 104 may continue to detect a condition of patient 101, thereby providing infusion device 102 with feedback data to continuously or periodically adjust a rate of insulin delivery in an automatic or autonomous manner based on the feedback data. In some examples, infusion device 102, monitoring device 104, and computing device 106 may be configured to utilize the closed-loop system only for a portion of the day, for example only when the patient is asleep or awake.

During operation, in some examples, computing device 106 may determine dosage commands that govern operation of infusion device 102. The dosage commands may include, but are not limited to, commands for delivering a basal dosage and/or a bolus dosage. An example basal dosage is an amount of insulin delivered to patient 101 to maintain glucose levels during periods of fasting, and an example bolus dosage is an amount of insulin (e.g., a meal bolus) delivered to patient 101 to regulate a rapid increase in glucose levels caused by consumption of a meal.

In some examples, the dosage commands may be based on patient-specific data. Examples of patient-specific data may include an insulin sensitivity factor, an active insulin time, and an insulin-to-carbohydrate ratio.

As will be described in greater detail below, in a closed-loop operating mode, computing device 106 may determine dosage commands based on a difference between a current glucose level in the body of the patient (e.g., received from monitoring device 104) and a target glucose level (e.g., determined by computing device 106). In this regard, the rate of insulin delivery may be related to the difference between the current glucose level and the target glucose level.

In some examples, infusion device 102 is configured to deliver a super bolus that includes an augmented bolus followed by a period of temporary basal dosage reduction (e.g., suspension). The augmented bolus may be an enlarged or supplemented meal bolus of insulin, and the period of temporary basal dosage reduction may include at least part of a postprandial period during which basal insulin is delivered in a reduced amount (e.g., a zero amount) or at a reduced rate (e.g., a rate of zero).

The amount of the augmented bolus can be determined in any of a variety of ways. For example, the amount of the augmented bolus may be determined by patient 101 and received at user interface 108 as user input. As another example, computing device 106 may, in response to a meal indication received at user interface 108, automatically determine the amount of the augmented bolus.

In some examples, the amount of the augmented bolus may be the sum of a meal bolus amount and a supplemental amount. The meal bolus amount may be determined using a bolus calculator, meal modeling, or other techniques for determining an amount of a bolus to compensate for the glucose increase expected to result from a meal (e.g., based on an amount of carbohydrates or other meal attributes). Hence, the meal bolus amount may correspond to an amount of insulin sufficient to counteract the glucose level increase expected to result from a meal. In contrast, the supplemental amount may correspond to an additional amount of insulin (e.g., an amount of insulin in excess of what is sufficient for counteracting the glucose level increase caused by a meal) which, when delivered with the meal bolus amount, mitigates the size of the spike in glucose level caused by a meal. In some examples, the supplemental amount may be determined based on predicting an amount of basal dosages that would otherwise have been delivered during at least part of a postprandial period. Thus, the supplemental amount may be, in effect, borrowed from the basal dosages. Additionally or alternatively, the supplemental amount may be determined based on averaging amounts of basal dosages that have historically been delivered during a historical time period similar to the at least part of the postprandial period In some examples, the supplemental amount may be determined based on applying a function (e.g., a percentage, a ratio, or a proportion) to the meal bolus amount. In some examples, the supplemental amount may be determined based on the meal bolus and a model utilizing the meal bolus and a basal insulin suspension period to determine a glucose level during the postprandial period.

In some examples, computing device 106 may be configured to automatically determine a duration of reduced basal dosage deliveries and cause infusion device 102 to reduce basal dosage deliveries for the determined duration. The duration of reduced basal dosage deliveries may be determined based on the supplemental amount. In some embodiments, the duration of reduced basal dosage deliveries may be determined based on using an active insulin time to calculate an amount of time for metabolizing the supplemental amount. In some embodiments, the duration of reduced basal dosage deliveries may be determined based on using the supplemental amount to calculate a number of basal dosage deliveries to forgo and/or an amount by which to reduce basal dosage deliveries. As used herein, the term "reduction" encompasses suspension, which may be considered to be a reduction to a zero value.

In some examples, the duration of reduced basal dosage deliveries may be determined by an insulin feedback (IFB) term of a closed-loop glucose control scheme. The IFB term may include a numeric value that accounts for the amount of insulin on-board (IOB) that has yet to be metabolized. Upon delivery of the augmented bolus, the IFB term of the closed-loop control process may cause infusion device 102 to automatically reduce postprandial basal dosage delivery. By accounting for IOB in the IFB term, the probability of insulin stacking may be reduced (e.g., to zero) so as to curtail or avoid over-delivery of insulin during the period of basal dosage reduction.

In some examples, computing device 106 may determine, based on a mathematical model, a probability metric representing the likelihood of a hypoglycemic event following delivery of the augmented bolus and automatically cause reduction of basal dosage deliveries for a postprandial duration of time that is influenced by the probability metric. For example, computing device 106 may cause infusion device 102 to reduce basal dosage deliveries until the probability of the hypoglycemic event is less than a threshold value, at which time computing device 106 may cause infusion device 102 to increase basal dosage deliveries.

As described herein, the bolus dosage of insulin delivered in connection with a meal may be automatically increased or otherwise adjusted while the infusion device is in an automated or autonomous operating mode to reduce the postprandial peak or rate of increase in the patient's glucose levels. Additionally, basal dosage deliveries in the autonomous operating mode may be automatically reduced for at least an initial portion of the postprandial period, thereby reducing the likelihood of potential over-delivery or postprandial hypoglycemia. Thus, the postprandial glycemic peak is reduced while also reducing the likelihood of postprandial hypoglycemia.

Although described as delivering insulin, in other examples, infusion system 100 may be configured to deliver one or more other fluids, liquids, gels, or medications to patient 101. Example fluids, liquids, gels may include, but are not limited to, a nutritional supplement, a dye, a tracing medium, a saline medium, a hydration medium, or the like. Example medications may include, but are not limited to, HIV drugs, drugs to treat pulmonary hypertension, iron chelation drugs, pain medications, anti-cancer treatments, vitamins, hormones, or the like.

Figure 2:
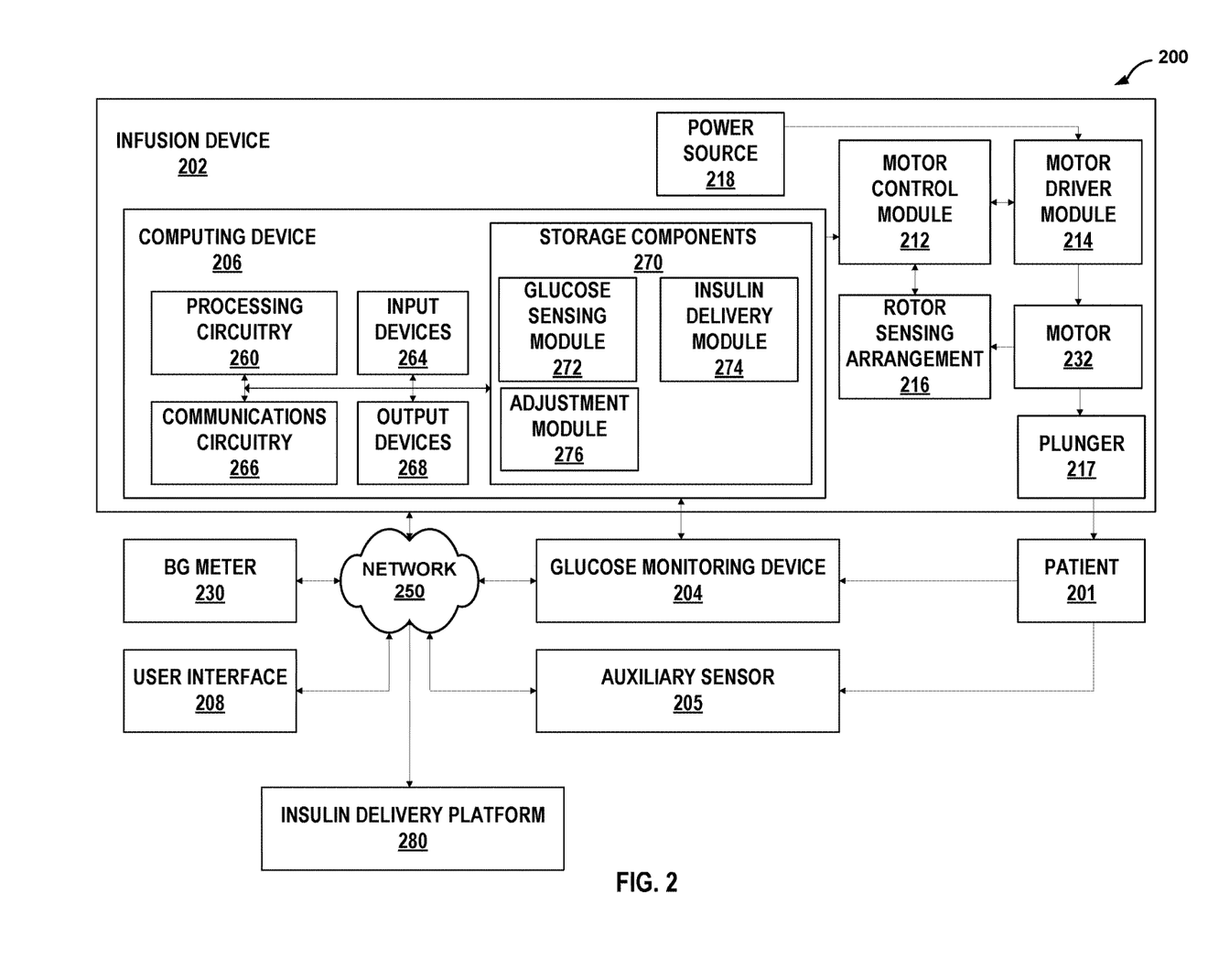
FIG. 2 is a schematic diagram illustrating an example of an insulin infusion system.

FIG. 2 depicts an example insulin infusion system 200 that includes infusion device 202, which may be similar or identical to infusion device 102. Insulin infusion system 200 may be configured to regulate a physiological condition in patient 201 toward a desired value (e.g. target value) or to maintain the physiological condition within a desired range of values in an automated or an autonomous manner. Insulin infusion system 200 may be the same or substantially similar to infusion system 100 described in reference to FIG. 1, except for the differences described herein. For example, like infusion system 100, insulin infusion system 200 includes an infusion device, a monitoring device, a computing device, and a user interface.

As illustrated in FIG. 2, infusion device 202 may be integrated with computing device 206. Each of infusion device 202 (e.g., including computing device 206), glucose monitoring device 204, and user interface 208 is optionally coupled to network 250. In some examples, fewer components (e.g., only computing device 206) may be coupled to network 250. Network 250 may include any public or private communication network, for instance, based on Bluetooth, WiFi®, a proprietary protocol for communicating with implantable medical devices, or other types of networks for transmitting data between computing systems, servers, and/or computing devices, both implanted within and located external to a patient. Infusion device 202 (e.g., including computing device 206), glucose monitoring device 204, and user interface 208 may each be communicatively coupled to network 250 using a respective network link, which may include any type of network connection, such as a wired or wireless connection. Network 250 may provide a device (e.g., infusion device 202, computing device 206, glucose monitoring device 204, and/or other components of system 200) with access to the Internet and/or may allow devices to communicate with each other.

Computing device 206 is configured to control operation of the insulin infusion device 202 according to one or more insulin delivery programs. Computing device 206 may include processing circuitry 260, one or more input devices 264, communications circuitry 266, one or more output devices 268, and one or more storage components 270. In some examples, computing device 206 maintains sets of instructions stored in the one or more storage components 270 (e.g., glucose sensing module 272, insulin delivery module 274, and adjustment module 276). In some examples, computing device 206 may include additional components or fewer components.

Processing circuitry 260 may include various types of hardware, including, but not limited to, one or more microprocessors, controllers, digital signal processors (DSPs), application specific integrated circuits (ASICs), field-programmable gate arrays (FPGAs), or equivalent discrete or integrated logic circuitry, as well as combinations of such components. The terms "processing circuitry" or "processors" may generally refer to any of the foregoing logic circuitry, alone or in combination with other logic circuitry, or any other equivalent circuitry. Processing circuitry 260 represents hardware that can be configured to execute firmware and/or software that sets forth one or more of the algorithms described herein. For example, processing circuitry 260 may be configured to implement functionality, process instructions, or both. In some examples, processing circuitry 260 may be configured to execute sets of instructions stored within one or more storage components 270. Examples of such sets of instructions include glucose sensing module 272 and insulin delivery module 274. In some examples, processing circuitry 260 includes processing circuitry of an implantable medical device and/or other devices of system 200 (e.g., infusion device 202, glucose monitoring device 204, or the like).

Computing device 206 also includes one or more input devices 264. Input devices 264, in some examples, are configured to receive input from a user through tactile, audio, or video sources. Examples of input devices 264 include a mouse, a button, a keyboard, a voice responsive system, video camera, microphone, touchscreen, or any other type of device capable of detecting a command from a user. In some example approaches, user interface 208 includes all input devices 264 employed by computing device 206.

Computing device 206 further includes communications circuitry 266. Computing device 206 may utilize communications circuitry 266 to communicate with external devices (e.g., glucose monitoring device 204, auxiliary sensor 205, user interface 208, and/or blood glucose meter 230) via network 250 and/or one or more wired or wireless networks. Communications circuitry 266 may include a communications interface, such as an Ethernet card, a radio frequency transceiver, cellular transceiver, a Bluetooth® interface card, USB interface, or any other type of device that can send and/or receive information. In some examples, computing device 206 utilizes communications circuitry 266 to wirelessly communicate with an external device such as a remote server system (e.g., insulin delivery platform 280).

Computing device 206 may further include one or more output devices 268. Output devices 268, in some examples, are configured to provide output to a user, for example, using audio, video or tactile media. For example, output devices 268 may include user interface 208, a sound card, a video graphics adapter card, or any other type of device for converting a signal into an appropriate form understandable to humans. In some example approaches, user interface 208 includes all output devices 268 employed by computing device 206.

One or more storage components 270 may be configured to store information within computing device 206 during operation. One or more storage components 270, in some examples, include one or more non-transitory processor-readable storage media or processor-readable storage devices. In some examples, one or more storage components 270 include a temporary memory, meaning that a primary purpose of one or more storage components 270 is not long-term storage. One or more storage components 270, in some examples, include a volatile memory, meaning that one or more storage components 270 does not maintain stored contents when power is not provided to one or more storage components 270. Examples of volatile memories include random access memories (RAM), dynamic random-access memories (DRAM), static random-access memories (SRAM), and other forms of volatile memories known in the art. In some examples, one or more storage components 270 are used to store program instructions for execution by processing circuitry 260. One or more storage components 270, in some examples, are used by software or firmware applications running on computing device 206 to temporarily store information during program execution.

In some examples, one or more storage components 270 may further include one or more storage components 270 configured for longer-term storage of information. In some examples, one or more storage components 270 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

As noted above, computing device 206 also may include glucose sensing module 272, insulin delivery module 274, and adjustment module 276. Each of glucose sensing module 272, insulin delivery module 274, and adjustment module 276 may be implemented in various ways. For example, glucose sensing module 272, insulin delivery module 274, and/or adjustment module 276 may be implemented as an application or a part of an application executed by processing circuitry 260. In some examples, glucose sensing module 272, insulin delivery module 274, and/or adjustment module 276 may be implemented as part of a hardware unit of computing device 206 (e.g., as circuitry).

Functions performed by glucose sensing module 272, insulin delivery module 274, and adjustment module 276 are explained in further detail below, and in reference to the example flow diagrams illustrated in FIGS. 4 and 5. In some examples, the features and/or functionality of the computing device 206, e.g., glucose sensing module 272, insulin delivery module 274, and/or adjustment module 276, may be at least partially implemented by a remote computing device or server, e.g., insulin delivery platform 280, that is physically distinct and/or separate from computing device 206.

In some examples, glucose monitoring device 204 includes one or more interstitial glucose sensing elements configured to output signals (e.g., electrical or optical signals) indicative of the interstitial fluid glucose level in patient 201. Glucose monitoring device 204 may filter or otherwise process the output signals to obtain values indicative of the interstitial fluid glucose level (e.g. sensor data). In some examples, glucose monitoring device 204 may be calibrated based on a measurement of blood glucose. For example, insulin infusion system 200 may include a blood glucose meter 230. Blood glucose meter 230 may include a device (e.g., a finger stick device) configured to obtain a blood sample. Computing device 206, or some other device that executes instructions such as those maintained as glucose sensing module 272, may be communicatively coupled to blood glucose meter 230 via network 250 and configured to use a blood glucose measurement as a reference glucose level for calibrating glucose monitoring device 204. In this way, the reference glucose level and values indicative of the interstitial fluid glucose level may be used to determine a calibrated glucose level (e.g., a sensor glucose level or a sensed glucose level).

In some examples, insulin infusion system 200 may include at least one auxiliary sensor 205. Auxiliary sensor 205 may be worn, carried, or operatively coupled to patient 201 to measure activity or physiological parameters of the patient that may influence the glucose levels or glycemic response of patient 201. Auxiliary sensor 205 may be a standalone component worn by the patient and/or may be integrated with infusion device 202 or glucose monitoring device 204. In some examples, auxiliary sensor 205 may include a heart rate sensor configured to detect a heart rate of patient 201. The heart rate of patient 201 may be indicative of exercise that may influence the glucose level or glycemic response of patient 201. In some examples, auxiliary sensor 205 may include an acceleration sensor configured to detect an acceleration of patient 201. The acceleration (or lack thereof) may be indicative of exercise, sleep, or some other condition of patient 201 that may influence the glycemic response of patient 201. In some examples, auxiliary sensor 205 may include an invasive, interstitial, and/or subcutaneous sensor configured to be inserted into the patient 201 to obtain measurements of other physiological conditions, such as a lactate level, a ketone level, or the like.

In some examples, auxiliary sensor 205 may include one or more environmental sensors to detect the current operating environment around infusion device 202. For example, the environmental sensors may include a temperature sensor, a humidity sensor, and/or a pressure sensor. In some examples, auxiliary sensor 205 may include a position sensor to detect the current geographic location of infusion system 200, such as a global positioning system (GPS) receiver.

Infusion device 202 includes motor control module 212, which may be coupled via motor driver module 214 to motor 232 or some other actuator configured to provide insulin to patient 201, for example, based on displacing plunger 217 in a reservoir. Motor 232 may be any suitable electric motor, such as a direct current (DC) motor or a brushless DC motor. Motor driver module 214 is coupled to power source 218 and motor 232. Motor control module 212 is coupled to motor driver module 214. In response to receiving, from computing device 206, a dosage command indicative of an amount of insulin and/or a rate of insulin delivery, motor control module 212 may generate and output one or more signals that operate motor driver module 214 to provide current from power source 218 to motor 232 to displace plunger 217. The dosage command may be based on a selected infusion delivery program. In some examples, the dosage command may be indicative of a bolus, such as a meal bolus.

In examples in which computing device 206 is configured to control insulin infusion device 202 in a closed-loop mode, computing device 206, or some other device that executes instructions such as those maintained as glucose sensing module 272, may determine a current glucose level and a target glucose level. The current glucose level may be determined based on sensor data received from glucose monitoring device 204, auxiliary sensor 205, and/or blood glucose meter 230. Computing device 206, or some other device that executes instructions such as those maintained as glucose sensing module 272, may determine the target glucose based on an upper glucose limit (e.g., a hyperglycemic threshold), a lower glucose limit (e.g., a hypoglycemic threshold), and/or a range of glucose levels. In some examples, computing device 206, or some other device that executes instructions such as those maintained as glucose sensing module 272, may store the target value, the upper glucose limit, the lower glucose limit, and/or the range of glucose levels. After determining the current glucose level and the target glucose level, computing device 206, or some other device that executes instructions such as those maintained as insulin delivery module 274, may determine dosage commands for delivering insulin to patient 201. The dosage commands, e.g., indicative of an amount of insulin to be delivered and/or a rate of insulin delivery, enable regulating the current glucose level toward the target glucose level. In some examples, the dosage commands may be based on the difference between a current glucose level and the target glucose level. Additionally, or alternatively, the dosage commands may be indicative of a meal bolus amount that is determined based on a meal indication, such as user input indicative of an amount of carbohydrates in a meal or a predicted amount of carbohydrates in a meal based on meal modeling. In this way, infusion device 202 may be configured to determine, in response to a meal indication, a meal bolus.

In some examples, computing device 206 may be configured to determine, in response to a meal indication, an augmented meal bolus. For example, adjustment module 276 may cause automatic adjustment of an insulin-to-carbohydrate ratio such that an enlarge bolus dosage is determined for a meal.

In some examples, computing device 206 may be configured to determine a duration of a postprandial period of reduced basal dosage deliveries. For example, the duration may be determined based on historical durations of glycemic response to historical augmented meal boluses, such as durations for a glucose level or IOB to return to a target level after a meal.

During operation, in response to receiving a dosage command from computing device 206 or some other device that executes instructions such as those maintained as insulin delivery module 274, motor control module 212 may determine a power level and a power supply duration. The power level and the power supply duration may be proportional to the amount of insulin to be delivered and/or the rate of insulin delivery. Motor driver module 214, in response to a signal indicative of the power level and the power supply duration, may deliver power from power source 218 to motor 232 at the determined power level and power supply duration. Motor 232 may drive plunger 217 to deliver to patient 201 the desired amount of insulin at the desired rate of insulin delivery.

Power source 218 may include any suitable power source. In some examples, power source 218 may include a rechargeable or non-rechargeable battery housed within infusion device 202. Power source 218 may be configured to provide direct current (DC) power. Motor driver module 214 may include any suitable combination of circuitry or hardware to convert the DC power into alternating current (AC) signals. The AC signals may be applied to respective phases of the stator windings of motor 232, thereby resulting in current flowing through the stator windings to generate a stator magnetic field and cause the rotor of motor 232 to rotate. For example, motor control module 212 may be configured to receive a dosage command from computing device 206, or some other device that executes instructions such as those maintained as insulin delivery module 274, to determine a commanded translational displacement of plunger 217, and to determine a rotation of motor 232 to achieve the commanded translational displacement of plunger 217. In some examples, motor control module 212 may determine, based on a current rotational position (e.g., orientation) of a rotor of motor 232 indicated by the output of rotor sensing arrangement 216, the appropriate sequence of AC signals to be applied to the respective phases of the stator windings to rotate the rotor by the desired amount of rotation from its current rotational position.

Motor control module 212 may include a general purpose processor, a microprocessor, a controller, a microcontroller, a state machine, a content addressable memory, an application specific integrated circuit, a field programmable gate array, any suitable fixed function or programmable logic device, discrete gate or transistor logic, discrete hardware components, or any combination thereof, designed to perform the functions described herein. In some examples, the motor control module 212 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory processor-readable medium, which is capable of storing programming instructions for execution by the motor control module 212. The processor-executable programming instructions, when read and executed by the motor control module 212, cause the motor control module 212 to perform or otherwise support the tasks, operations, functions, and processes described herein. In some examples, the features and/or functionality of the motor control module 212 may be implemented by or otherwise integrated into the computing device 206, or vice versa.

Figure 3:
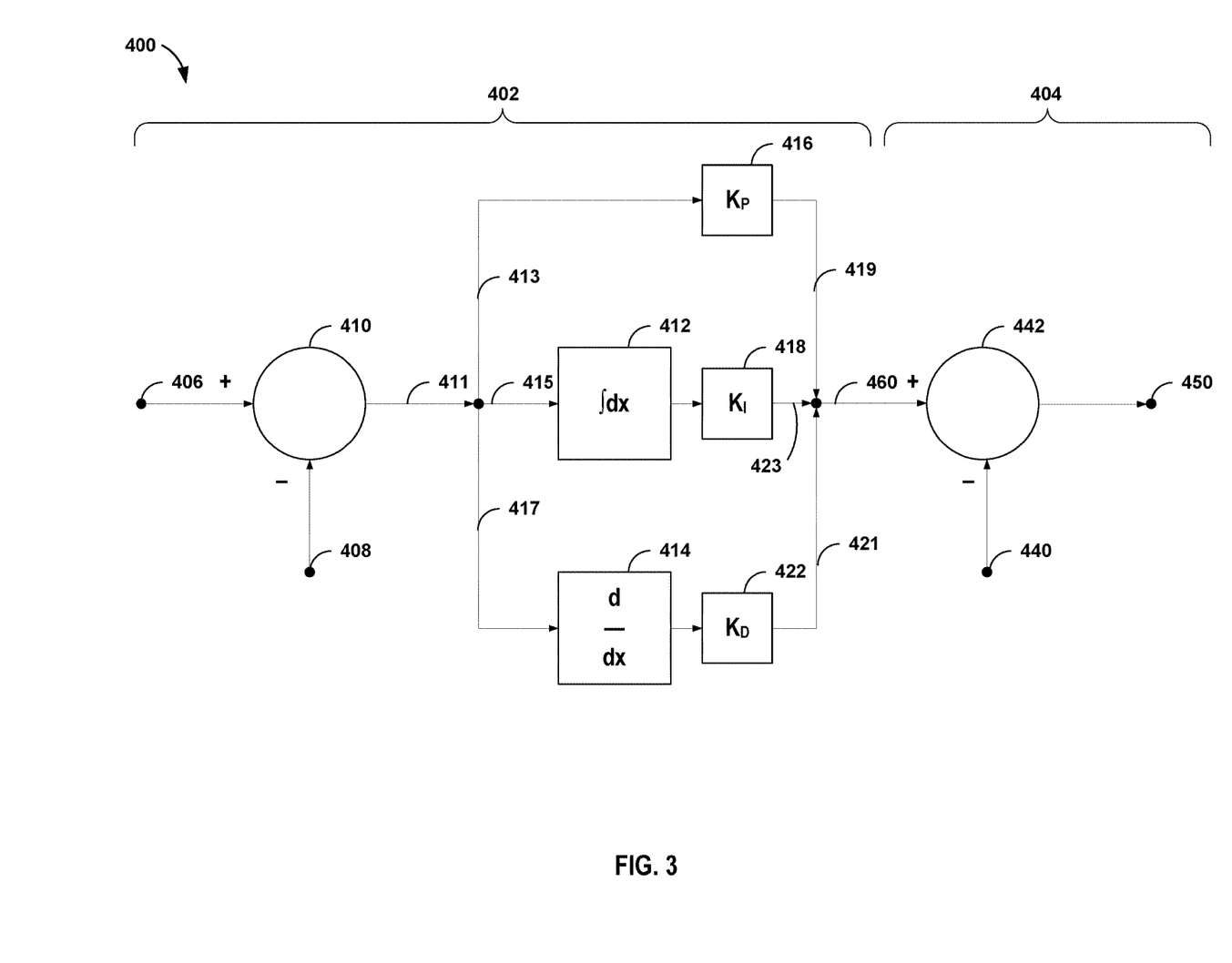
FIG. 3 is a schematic diagram illustrating an example closed-loop control system.

FIG. 3 is a schematic diagram illustrating an example closed-loop control system 400 that may be implemented by computing device 206, such as by execution of instructions maintained as one or more modules in storage components 270, to automatically or autonomously regulate a glucose level of a patient toward a target glucose level. Closed-loop control system 400 includes proportional-integral-derivative (PID) controller 402 that is configured to determine dosage commands for operating motor 232 based at least in part on the difference between current glucose level 406 and target glucose level 408. In some examples, PID controller 402 attempts to minimize the difference between current glucose level 406 and target glucose level 408.

For example, PID controller 402 may take, as input, target glucose level 408. In some examples, glucose sensing module 272 may determine target glucose level 408 based on one or more patient-specific parameters. In some other examples, PID controller 402 may obtain target glucose level 408 from an external device, such as insulin delivery platform 280. In some examples, computing device 206, or some other device that executes instructions such as those maintained as glucose sensing module 272, may store target glucose level 408. Additionally, PID controller 402 receives, as input, current glucose level 406, e.g., as provided by glucose monitoring device 204.

Closed-loop control system 400 includes a summation block 410 configured to determine error term 411 which is equal to the difference between target glucose level 408 and current glucose level 406. Error term 411 is provided to each of proportional term path 413, integral term path 415, and derivative term path 417. Within each of proportional term path 413, integral term path 415, and derivative term path 417, PID control parameters are applied to error term 411.

Proportional term path 413 includes gain block 416. In some examples, gain block 416 multiplies error term 411 by a proportional gain coefficient, $K_P$, to produce proportional term 419. The value of Kr may affect the rate of error term reduction, e.g., a larger $K_P$ may have a greater or more rapid effect on target glucose level 408 relative to a smaller $K_P$.

Derivative term path 417 includes derivative block 414 that determines the derivative of error term 411. The derivative of error term 411 may be indicative of a rate of change of error term 411 over time and, in some examples, indicative of a future error in target glucose level 408. Derivative term path 417 also includes gain block 422 that multiplies the derivative of error term 411 by a derivative gain coefficient, $K_D$, to produce derivative term 421.

Integral term path 415 includes integration block 412 that determines the integral of error term 411. The integral of error term 411 may be indicative of the sum of past error terms. Integral term path 415 includes gain block 418 that multiplies the integrated error term by an integral gain coefficient, $K_I$, to obtain integral term 423. In some examples, upper and lower limits may be applied to the integral term to curtail or prevent integral windup while providing basal dosage deliveries at steady-state conditions (e.g., when error term 411 has a zero value). For reference, example implementations are described in greater detail in U.S. Patent Pub. No. 2014/0066889. The proportional term, the constrained integral term, and the derivative term may be added or otherwise combined to obtain a value of PID delivery command 460 as output. The value of PID delivery command 460 may include an absolute value, such as an increment rounded or truncated to a pump delivery resolution, e.g., an increment of 0.025 units. In some examples, the PID delivery command may include an upper limit to prevent insulin stacking.

In some examples, the closed-loop PID gain coefficients ($K_P$, $K_I$, $K_D$) and potentially other control parameters (e.g., time constants or the like) may be calculated or otherwise determined using historical insulin delivery data. The historical insulin delivery data may include, but is not limited to, a type of insulin delivered, bolus amounts, timings of previous boluses, correction bolus information, glycemic response, current (historical) glucose levels, reference glucose levels, meal indications, patient-input events (e.g., exercise), or other information related to insulin delivery.

In some embodiments, one or more patient-specific parameters may be utilized to compensate, correct, or otherwise adjust the PID gain coefficients to account for various operating conditions experienced and/or exhibited by infusion device 202. The one or more patient-specific parameters may include, for example, an insulin sensitivity factor, a daily insulin requirement, an insulin limit, a reference basal rate, a reference fasting glucose, an active insulin action duration, pharmacodynamic time constants, or the like.

The PID gain coefficients may be stored in storage components 270. In some examples, storage components 270 may include a plurality of registers each associated with a respective control parameter for the PID control. For example, a first parameter register may store the target glucose level and be accessed by or otherwise associated with summation block 410, and similarly, a second parameter register accessed by proportional gain block 416 may store the proportional gain coefficient, a third parameter register accessed by integration gain block 418 may store the integration gain coefficient, and a fourth parameter register accessed by derivative gain block 422 may store the derivative gain coefficient. Various implementation details pertaining to closed-loop PID control and determining gain coefficients are described in greater detail in U.S. Pat. No. 7,402,153, which is incorporated by reference in its entirety.

In some examples, closed-loop control system 400 includes insulin feedback (IFB) portion 404. IFB portion 404 may be configured to adjust the value of PID delivery command 460 to compensate for insulin already delivered to the patient, e.g., insulin on board (JOB). By compensating for JOB, insulin over-delivery may be curtailed or avoided. IFB portion 404 includes a summation block 442 configured to determine a difference between the value of PID delivery command 460 and insulin feedback (IFB) term 440 to determine a value of insulin-compensated closed-loop delivery command 450. Motor control module 212, in response to a signal indicative of insulin-compensated closed-loop delivery command 450, may operate motor 232 to deliver insulin to the patient to regulate the glucose level toward target glucose level 408. Thus, closed-loop control system 400 may reduce the difference between a measured glucose level (e.g., a subsequently measured glucose level) and target glucose level 408 in a manner that accounts for the amount of IOB that has yet to be metabolized by the patient.

Still referring to FIG. 3 with continued reference to FIGS. 1-2, in one or more examples, IFB term 440 may be determined by motor control module 212 and/or processing circuitry 260. Historical insulin delivery information (e.g., respective amounts and timings of previous dosages) may be maintained or otherwise stored in storage components 270 and analyzed by processing circuitry 260 and/or motor control module 212 to estimate or otherwise determine insulin feedback term 440 as a function of historical insulin delivery information using pharmacokinetic models to estimate or otherwise calculate the amount of active insulin remaining in the subcutaneous, plasma, and effect site compartments. For example, the amount of active insulin remaining in the respective compartments at a sampling time k may be governed by the following Equations (1), (2), and (3):

$$I_S(k) = a_{11} \cdot I_s(k-1) + b_1 \cdot I_D(k); \tag{1}$$

$$I_P(k) = a_{21} \cdot I_S(k-1) + a22 \cdot I_P(k-1) + b_2 \cdot I_D(k); \text{ and} \tag{2}$$

$$I_E(k) = a_{31} \cdot I_S(k-1) + a_{32} \cdot I_P(k-1) + a_{33} \cdot I_E(k-1) + b_3 \cdot I_D(k), \tag{3}$$

where $I_S$ is the insulin in the subcutaneous compartment, $I_P$ is the insulin in the plasma compartment, $I_E$ is the effective insulin compartment, and $I_D(k)$ represents the amount of insulin delivered at time k, where the remaining a and b terms represent numerical constants, the derivation or determination of which are not germane to this disclosure, and which may be described in greater detail in, for example, United States Patent Application Publication Nos.: 2014/0066887 and 2014/0066889. In some examples, the $I_D(k)$ term includes both bolus dosages delivered independently of closed-loop control system 400 as well as automated basal dosages that were determined by closed-loop control system 400.

In examples in which insulin delivery is suspended or otherwise reduced at time k, $I_D(k)=0$. The amounts of IOB remaining in the subcutaneous, plasma, and effective insulin compartments may be added or otherwise combined to arrive at the cumulative insulin feedback term 440 at time k using the following equation: $IFB(k)=\gamma_1 \cdot I_S(k) + \gamma_2 \cdot I_P(k) + \gamma_3 \cdot I_E(k)$, where $\gamma_1$, $\gamma_2$, or $\gamma_3$ represent numerical constants, the derivation or determination of which are not germane to this disclosure, and which may be described in greater detail in, for example, United States Patent Application Publication Nos.: 2014/0066887 and 2014/0066889. IFB term 440 is provided to summation block 442 and subtracted from the value of PID delivery command 460 at time k to obtain the value of insulin-compensated closed-loop delivery command 450.

The value of PID delivery command 460 at time k may be governed by the equation: $PID(k) = K_P*Err(k) + K_D*dErr(k)/dt + K_I*Int(k)$, where $Err(k)$ represents the difference between the patient's current (or most recent) glucose measurement at time k and the target glucose measurement (e.g., the output of block 410) and $Int(k)$ represents the integral term governed by the equation $Int(k)=Int(k-1)+c1*Err(k)$, where c1 is a constant. As described above, the $Int(k)$ term may be limited to curtail or prevent windup and/or maintain basal dosage delivery at steady-state conditions (e.g., when $Err(k)=0$).

The value of insulin-compensated closed-loop delivery command 450 may be equal to zero when IFB term 440 is greater than the value of PID delivery command 460. Thus, insulin delivery may be reduced at some sampling times.

Increasing the amount of insulin delivered (e.g., based on generating an augmented bolus) may result in an increased value of IFB term 440. This may cause an increase in the duration and/or probability of IFB term 440 exceeding the value of PID delivery command 460, even as current glucose level 406 increases. For example, augmenting a meal bolus may result in automatically reducing, by closed-loop control system 400, basal dosage deliveries for at least part of a postprandial period, thereby reducing the probability or likelihood of postprandial hypoglycemia or over-delivery. In some embodiments, closed-loop control system 400 may automatically increase basal dosage deliveries when current glucose level 406 increases sufficiently relative to target glucose level 408 to result in a PID delivery command value that is greater than the insulin feedback term 440. In some examples, closed-loop control system 400 may automatically resume basal insulin delivery when the IOB is sufficiently metabolized to reduce IFB term 440 below the PID delivery command value.

While the subject matter is described above in the context of an insulin feedback term calculated using fixed numerical constants for the a and b terms, in other examples, the a and b terms in the insulin feedback equations may be determined in a patient-specific manner to reflect a patient-specific pharmacokinetic or pharmacodynamic response. In some examples, a patient-specific IFB term may be dynamically determined and utilized as IFB term 440.

Figure 4:
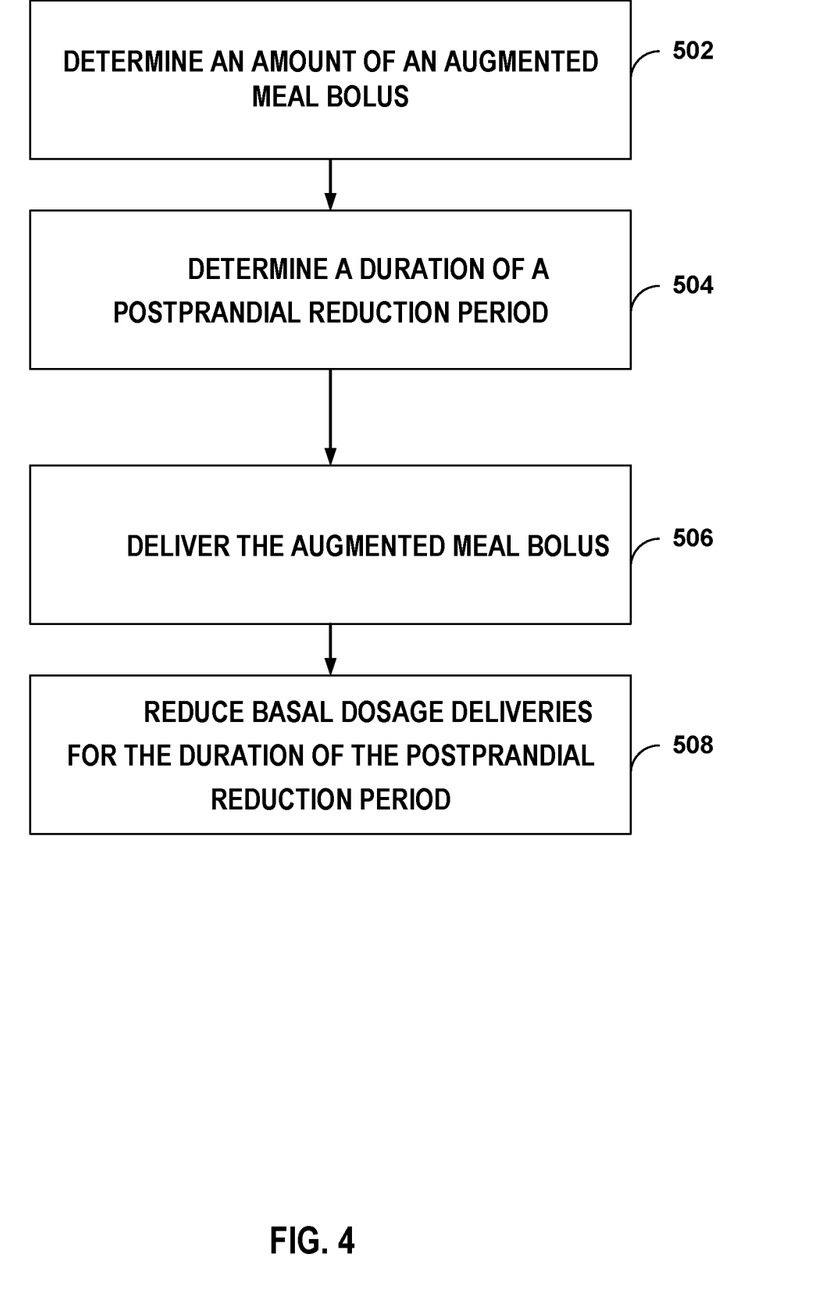
FIG. 4 is a flow diagram illustrating an example process for automatically generating a super bolus.

FIG. 4 is a flow diagram illustrating an example process for automatically generating a super bolus. The techniques illustrated in FIG. 4 may be suitable for implementation in connection with an autonomous operating mode of an infusion device to facilitate postprandial glucose management, for example, by reducing the postprandial peak glucose level and/or reducing the probability of postprandial hypoglycemia. Although the techniques illustrated in FIG. 4 are described in reference to insulin infusion system 200 and closed-loop control system 400, in some examples, the techniques may be performed using one or more different systems.

The techniques illustrated in FIG. 4 include determining an amount of an augmented meal bolus to be delivered to a patient for regulating the patient's glycemic response to a meal (502). As suggested by its name, an augmented meal bolus may be a meal bolus that has been augmented such that the amount of the augmented meal bolus exceeds a sufficient amount for counteracting a glucose level increase caused by a meal. Stated differently, the amount of the augmented meal bolus may include an amount that is sufficient for metabolizing a meal as well as a supplementary amount in excess of what is sufficient for metabolizing the meal. The amount of the augmented bolus may be determined in any of a variety of ways. For example, processing circuitry 260 may determine the amount of the augmented meal bolus as a whole or in portions.

In some embodiments, a patient-specific parameter may be adjusted to holistically determine the amount of the augmented meal bolus. For example, processing circuitry 260 may determine the amount of the augmented meal bolus based on scaling an insulin-to-carbohydrate ratio (e.g., 1:10) by a reduction factor (e.g., 0.8) and multiplying this scaled ratio (e.g., 1:8) to an approximate amount of carbohydrates included in a meal (e.g., an amount of carbohydrates obtained as user input). This may cause an increase in the size of the meal bolus that would otherwise have been calculated.

In some other embodiments, different portions of the augmented meal bolus may be separately determined and added together. For example, processing circuitry 260 may concurrently determine an unaugmented meal bolus amount and an excess amount to be aggregated to yield the amount of the augmented meal bolus. The unaugmented meal bolus amount may correspond to a bolus dosage that would otherwise have been determined for mealtime delivery (e.g., immediately before, concurrently with, and/or immediately after a meal), and the excess amount may correspond to basal dosages that would otherwise have been determined for postprandial delivery (e.g., during a fasting period immediately following a meal).

The unaugmented meal bolus amount may be determined in any of a variety of ways. In some embodiments, this amount may be determined using a bolus calculation program. For example, the bolus calculation program may take as input the size, ingredients, and/or other attributes of a meal and provide as output an amount of insulin that will be sufficient for metabolizing the meal. In some embodiments, the unaugmented meal bolus amount may be determined using a physiological model of patient 201. For example, the physiological model may include one or more equations having patient-specific parameters (e.g., insulin sensitivity factor and/or insulin-to-carbohydrate ratio) for predicting a glycemic response to the meal and for predicting an amount of insulin that will be sufficient for counteracting the glycemic response. In some embodiments, the unaugmented meal bolus amount may be determined based on user input. For example, an estimated amount of carbohydrates included in a meal may be received via user interface 208 and provided as input to a bolus calculation program and/or a physiological model.

The excess amount may also be determined in any of a variety of ways. In some embodiments, the excess amount may be determined based on applying a function to the unaugmented meal bolus amount. For example, the excess amount may be determined based on applying a percentage, a ratio, or a proportion to the unaugmented meal bolus amount. In some embodiments, the excess amount may be determined based on insulin delivery data for historical time periods. For example, the excess amount may be determined based on calculating a total amount of basal dosages deliveries during a postprandial time period for a previous meal. As another example, the excess amount may be determined based on calculating an average rate of basal dosage deliveries during a postprandial time period for a previous meal and multiplying the average rate to a predetermined duration (e.g., a duration determined at 504).

The techniques illustrated in the example of FIG. 4 include determining a duration of a postprandial reduction period during which basal dosage deliveries to the patient are to be reduced (e.g., to a zero or a non-zero value) (504). The duration may be determined in any of a variety of ways. In some embodiments, the duration may have a predetermined value. For example, basal dosage deliveries may be reduced (e.g., suspended) for a predetermined period of two hours after a meal. In some embodiments, the duration may be determined based on using an active insulin time to calculate an amount of time for metabolizing the excess amount. For example, if the active insulin time for two units of insulin is two hours and if the excess amount is one unit of insulin, then the amount of time for metabolizing the excess amount would be one hour, and basal dosage deliveries may be suspended or otherwise reduced for one hour after a meal. Although described as a linear decay of insulin activity, in other examples, the decay of insulin activity may be nonlinear, such as exponential or the like. In some embodiments, the duration may be determined based on using the excess amount to calculate a number of basal dosage deliveries to reduce (e.g., forgo). For example, if the excess amount is calculated to be one unit of insulin and if the average rate of basal dosage deliveries immediately preceding a meal is calculated to be 0.1 units of insulin every five minutes, then the number of basal dosage deliveries to forgo would be determined to be ten, which may correspond to a duration of fifty minutes. Alternatively, instead of forgoing ten basal dosage deliveries, forty basal dosage deliveries may be reduced by 75% (e.g., each basal dosage delivery may be reduced to a minimal rate of 0.025 units every five minutes), which may correspond to a duration of 200 minutes.

The techniques illustrated in the example of FIG. 4 include delivering the augmented meal bolus to patient 201 in the amount determined at 502 (506). For example, processing circuitry 260 may cause performance of 506 at insulin infusion device 202 based on generating a signal (e.g., a command signal) that is communicated to device 202. The signal may be indicative of the amount of the augmented meal bolus.

The techniques illustrated in the example of FIG. 4 also include reducing basal dosage deliveries for the duration of the postprandial reduction period determined at 504 (508). For example, processing circuitry 260 may cause performance of 508 at insulin infusion device 202 based on generating a signal (e.g., a command signal) that is communicated to device 202. The signal may be indicative of reduced (e.g., disabled) insulin delivery. Additionally or alternatively, the signal may be indicative of the duration of the postprandial reduction period. The signal may be the same signal discussed above or a different signal.

In some embodiments, basal dosage deliveries may thereafter be increased (e.g., re-enabled). For example, processing circuitry 260 may generate a signal (e.g., a command signal) indicative of increased basal dosage deliveries, and the signal may be communicated to insulin infusion device 202. In some embodiments, the basal dosage deliveries may be increased to an amount or rate used prior to the meal. For example, after processing circuitry 260 causes suspension of basal dosage deliveries, it may cause resumption of basal dosage deliveries.

Figure 5:
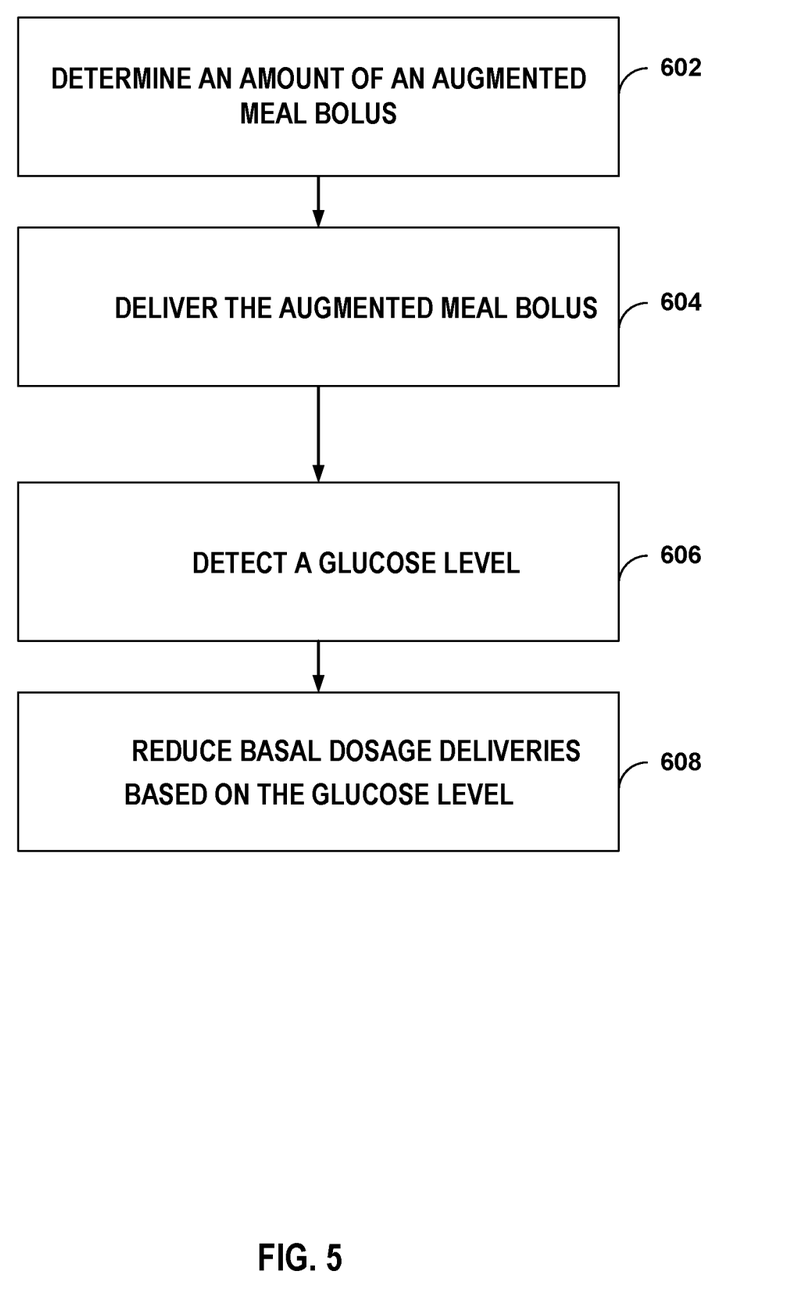
FIG. 5 is a flow diagram illustrating another example process for automatically generating a super bolus.

FIG. 5 is a flow diagram illustrating another example process for automatically generating a super bolus. The techniques illustrated in FIG. 5 may be suitable for implementation in connection with an autonomous operating mode of an infusion device to improve postprandial glucose management, for example, by reducing the postprandial peak glucose level and/or reducing the probability of postprandial hypoglycemia. Although the techniques illustrated in FIG. 5 are described in reference to insulin infusion system 200 and closed-loop control system 400, in some examples, the technique may be performed using one or more different systems.

The techniques illustrated in FIG. 5 include determining an amount of an augmented meal bolus (602). 602 of FIG. 5 may be similar or identical to 502 of FIG. 4.

The techniques illustrated in FIG. 5 also include delivering the augmented bolus to patient 201 in the amount determined at 602 (604). 604 of FIG. 5 may be similar or identical to 506 of FIG. 4.

The techniques illustrated in FIG. 5 also include detecting a glucose level of patient 201 (606). For example, 606 may be performed at glucose monitoring device 204, and processing circuitry 260 may obtain the detected glucose level from device 204. The detected glucose level may be indicative of a glycemic response to the augmented meal bolus. In some embodiments, 606 may be periodically performed at predetermined time intervals.

The techniques illustrated in FIG. 5 also include reducing basal dosage deliveries to patient 201 based on the detected glucose level (608). For example, processing circuitry 260 may cause performance of 608 at insulin infusion device 202. If insulin delivery is not already reduced (e.g., disabled), processing circuitry 260 may generate a signal (e.g., a command signal) indicative of reduced insulin delivery, and the signal may be communicated to device 202.

In some embodiments, basal dosage deliveries may be reduced based on the detected glucose level and the value of an insulin feedback (IFB) term. For example, processing circuitry 260 may determine an IFB term value based on the amount of the augmented meal bolus, determine a closed-loop delivery command value based on the difference between the detected glucose level and a target glucose level, and compare the IFB term value with the difference to dynamically determine whether or not to cause/maintain reduction of basal dosage deliveries. Basal dosage deliveries may be reduced when the IFB term value is greater than the difference.

In some embodiments, basal dosage deliveries may be reduced based on the detected glucose level and a probability of postprandial hypoglycemia. For example, processing circuitry 260 may provide the detected glucose level as input to a mathematical model to determine a probability of postprandial hypoglycemia, compare the probability to a predetermined threshold value, and dynamically determine whether or not to cause/maintain reduction of basal dosage deliveries. Basal dosage deliveries may be reduced when the probability exceeds the predetermined threshold value. The probability may be determined based on various data including a current glucose level, a current rate of change in glucose level, a current amount of active insulin, and/or an estimated amount of carbohydrates included in a meal.

In some embodiments, the example process of FIG. 5 may be partially iterative. For example, 608 may loop back to 606 until conditions have changed such that 606 no longer proceeds to 608 (e.g., basal dosage deliveries can be increased). In some embodiments, basal dosage deliveries may be increased based on a second glucose level and a smaller IFB term value. For example, processing circuitry 260 may generate a signal (e.g., a command signal) indicative of increased basal dosage delivery upon determining that the smaller IFB term value is less than the difference between the second glucose level and a target glucose level. In some embodiments, basal dosage deliveries may be increased based on a second glucose level and a second probability of postprandial hypoglycemia. For example, processing circuitry 260 may generate a signal (e.g., a command signal) indicative of increased basal dosage delivery upon determining that the second probability does not exceed the predetermined threshold value.

It should be appreciated that each of the example processes discussed above may be modified to include any number of additional or alternative tasks. For example, prior to determining an amount of an augmented bolus, processing circuitry 260 may detect occurrence of a meal (e.g., via user input or automatically based on contextual data indicative of a meal). Furthermore, the tasks need not be performed in the order depicted in the figures (e.g., 502 and 504 may be performed concurrently or 504 may be performed prior to 502).

Various examples of the disclosure have been described. Any combination of the described systems, operations, or functions is contemplated. These and other examples are within the scope of the following claims.

What is claimed is:

1. A system for automatically generating a super bolus, the system comprising:
   one or more processors; and
   one or more processor-readable storage media storing instructions which, when executed by the one or more processors, cause performance of:
      determining an amount of an augmented meal bolus to be delivered to a patient for regulating the patient's glycemic response to a meal, the amount of the augmented meal bolus exceeding a sufficient amount for counteracting a glucose level increase caused by the meal;
      determining a duration of a postprandial reduction period during which basal dosage deliveries to the patient are to be reduced; and
      after determining the amount of the augmented meal bolus and the duration of the postprandial reduction period, causing:
         delivery of the augmented meal bolus to the patient in the determined amount, and
         reduction of basal dosage deliveries to the patient for the duration of the postprandial reduction period.

2. The system of claim 1, wherein determining the duration of the postprandial reduction period comprises:
   calculating an excess amount by which the amount of the augmented meal bolus exceeds the sufficient amount; and
   calculating, based on the excess amount, a number of basal dosage deliveries to forgo.

3. The system of claim 1, wherein determining the duration of the postprandial reduction period comprises:
   calculating an excess amount by which the amount of the augmented meal bolus exceeds the sufficient amount; and
   calculating, based on an active insulin time, an amount of time for metabolizing the excess amount.

4. The system of claim 1, wherein determining the amount of the augmented meal bolus comprises:
   obtaining an amount of carbohydrates included in the meal; and
   multiplying an adjusted insulin-to-carbohydrate ratio to the amount of carbohydrates included in the meal.

5. The system of claim 1, wherein determining the amount of the augmented meal bolus comprises calculating an excess amount to be added to the sufficient amount based on:
   determining an average rate of basal dosage deliveries during a historical time period; and
   multiplying the average rate of basal dosage deliveries to a predetermined duration.

6. The system of claim 1, wherein determining the amount of the augmented meal bolus comprises calculating an excess amount to be added to the sufficient amount based on determining a total amount of basal dosage deliveries during a historical time period.

7. The system of claim 1, wherein the one or more processor-readable storage media further store instructions which, when executed by the one or more processors, cause performance of:
prior to determining the amount of the augmented meal bolus, detecting occurrence of the meal.

8. A processor-implemented method for automatically generating a super bolus, the method comprising:
determining an amount of an augmented meal bolus to be delivered to a patient for regulating the patient's glycemic response to a meal, the amount of the augmented meal bolus exceeding a sufficient amount for counteracting a glucose level increase caused by the meal;
determining a duration of a postprandial reduction period during which basal dosage deliveries to the patient are to be reduced; and
after determining the amount of the augmented meal bolus and the duration of the postprandial reduction period, causing:
delivery of the augmented meal bolus to the patient in the determined amount, and
reduction of basal dosage deliveries to the patient for the duration of the postprandial reduction period.

9. The method of claim 8, wherein determining the duration of the postprandial reduction period comprises:
calculating an excess amount by which the amount of the augmented meal bolus exceeds the sufficient amount; and
calculating, based on the excess amount, a number of basal dosage deliveries to forgo.

10. The method of claim 8, wherein determining the duration of the postprandial reduction period comprises:
calculating an excess amount by which the amount of the augmented meal bolus exceeds the sufficient amount; and
calculating, based on an active insulin time, an amount of time for metabolizing the excess amount.

11. The method of claim 8, wherein determining the amount of the augmented meal bolus comprises:
obtaining an amount of carbohydrates included in the meal; and
multiplying an adjusted insulin-to-carbohydrate ratio to the amount of carbohydrates included in the meal.

12. The method of claim 8, wherein determining the amount of the augmented meal bolus comprises calculating an excess amount to be added to the sufficient amount based on:
determining an average rate of basal dosage deliveries during a historical time period; and
multiplying the average rate of basal dosage deliveries to a predetermined duration.

13. The method of claim 8, wherein determining the amount of the augmented meal bolus comprises calculating an excess amount to be added to the sufficient amount based on determining a total amount of basal dosage deliveries during a historical time period.

14. The method of claim 8, further comprising:
prior to determining the amount of the augmented meal bolus, detecting occurrence of the meal.

15. One or more non-transitory processor-readable storage media storing instructions which, when executed by one or more processors, cause performance of:
determining an amount of an augmented meal bolus to be delivered to a patient for regulating the patient's glycemic response to a meal, the amount of the augmented meal bolus exceeding a sufficient amount for counteracting a glucose level increase caused by the meal;
determining a duration of a postprandial reduction period during which basal dosage deliveries to the patient are to be reduced; and
after determining the amount of the augmented meal bolus and the duration of the postprandial reduction period, causing:
delivery of the augmented meal bolus to the patient in the determined amount, and
reduction of basal dosage deliveries to the patient for the duration of the postprandial reduction period.

16. The one or more non-transitory processor-readable storage media of claim 15, wherein determining the duration of the postprandial reduction period comprises:
calculating an excess amount by which the amount of the augmented meal bolus exceeds the sufficient amount; and
calculating, based on the excess amount, a number of basal dosage deliveries to forgo.

17. The one or more non-transitory processor-readable storage media of claim 15, wherein determining the duration of the postprandial reduction period comprises:
calculating an excess amount by which the amount of the augmented meal bolus exceeds the sufficient amount; and
calculating, based on an active insulin time, an amount of time for metabolizing the excess amount.

18. The one or more non-transitory processor-readable storage media of claim 15, wherein determining the amount of the augmented meal bolus comprises:
obtaining an amount of carbohydrates included in the meal; and
multiplying an adjusted insulin-to-carbohydrate ratio to the amount of carbohydrates included in the meal.

19. The one or more non-transitory processor-readable storage media of claim 15, wherein determining the amount of the augmented meal bolus comprises calculating an excess amount to be added to the sufficient amount based on:
determining an average rate of basal dosage deliveries during a historical time period; and
multiplying the average rate of basal dosage deliveries to a predetermined duration.

20. The one or more non-transitory processor-readable storage media of claim 15, wherein determining the amount of the augmented meal bolus comprises calculating an excess amount to be added to the sufficient amount based on determining a total amount of basal dosage deliveries during a historical time period.

* * * * *